(12) United States Patent
Lederkremer

(10) Patent No.: US 7,981,627 B2
(45) Date of Patent: Jul. 19, 2011

(54) METHODS FOR DIAGNOSING AND MONITORING LIVER DISEASES

(75) Inventor: Gerardo Zelmar Lederkremer, Shoham (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 12/503,881

(22) Filed: Jul. 16, 2009

(65) Prior Publication Data

US 2010/0041069 A1    Feb. 18, 2010

Related U.S. Application Data

(60) Provisional application No. 61/129,760, filed on Jul. 17, 2008.

(51) Int. Cl.
*G01N 33/53* (2006.01)

(52) U.S. Cl. .......................... 435/7.1; 435/7.2; 436/518

(58) Field of Classification Search .................. None
See application file for complete search history.

(56) References Cited

U.S. PATENT DOCUMENTS

| | | | |
|---|---|---|---|
| 4,036,945 A | 7/1977 | Haber | |
| 4,331,647 A | 5/1982 | Goldenberg | |
| 4,816,567 A | 3/1989 | Cabilly et al. | |
| 4,946,778 A | 8/1990 | Ladner et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 2006/0286615 A1 | 12/2006 | Lederkremer et al. | |

FOREIGN PATENT DOCUMENTS

| | | |
|---|---|---|
| EP | 0773289 | 8/1996 |
| WO | WO 2004/081029 | 9/2004 |

OTHER PUBLICATIONS

Negi et al. Arch. Surg. 2004 vol. 139, p. 299-303.*
Official Action Dated Aug. 1, 2008 From the US Patent and Trademark Office Re.: U.S. Appl. No. 11/224,148.
Official Action Dated Feb. 7, 2008 From the US Patent and Trademark Office Re.: U.S. Appl. No. 11/224,148.
Communication Pursuant to Article 94(3) EPC Dated Aug. 21, 2009 From the European Patent Office Re.: Application No. 04720548.9.
International Preliminary Report on Patentability Dated Jun. 26, 2008 From the International Bureau of WIPO Re.: Application No. PCT/IL2004/000244.
International Search Report Dated Dec. 18, 2007 From the International Searching Authority Re.: Application No. PCT/IL04/00244.
Invitation to Pay Additional Fees Dated Mar. 14, 2007 From the International Searching Authority Re.: Application No. PCT/IL04/00244.

(Continued)

*Primary Examiner* — Jacob Cheu

(57) ABSTRACT

A method of diagnosing a liver disorder in a subject is disclosed. The method comprises determining a level of sH2A and at least one additional liver marker in a sample of the subject wherein a change beyond a predetermined threshold in both the sH2A and the at least one additional marker with respect to a sample from a healthy individual is indicative of the liver disorder. Kits for diagnosing a liver disorder are also disclosed.

6 Claims, 3 Drawing Sheets

OTHER PUBLICATIONS

Official Action Dated Dec. 14, 2007 From the US Patent and Trademark Office.: U.S. Appl. No. 11/224,148.
Official Action Dated Mar. 20, 2009 From the US Patent and Trademark Office Re.: U.S. Appl. No. 11/224,148.
Official Action Dated Aug. 21, 2009 From the US Patent and Trademark Office Re.: U.S. Appl. No. 11/224,148.
Response Dated Dec. 16, 2009 to Communication Pursuant to Article 94(3) EPC of Aug. 21, 2009 From the European Patent Office Re.: Application No. 04720548.9.
Supplementary European Search Report Dated Jun. 8, 2009 From the European Patent Office Re.: Application No. 04720548.9.
Written Opinion Dated Dec. 18, 2007 From the International Searching Authority Re.: Application No. PCT/IL04/00244.
Bischoff et al. "The H1 and H2 Polypeptides Associate to Form the Asialoglycoprotein Receptor in Human Hepatoma Cells", The Journal of Cell Biology, XP007898593, 106(4): 1067-1974, Apr. 1988. p. 1068, l-h Col., Last §-r-h Col., § 1.
Campbell "General Properties and Applications of Monoclonal Antibodies", Monoclonal Antibody Technology, Elsevier Science Publishers, Chap.1: 1-32, 1984. p. 29.
Doyle et al. "Plasma Membrane: Biogenesis and Turnover", The Liver: Biology and Pathobiology, 2nd Ed.(Chap.8): 141-163, 1988.
Drickamer "Clearing Up Glycoprotein Hormones", Cell, 67: 1029-1032, 1991.
Gopal et al. "Abnormal Findings on Liver Function Tests: Interpreting Results to Narrow the Diagnosis and Establish a Prognosis", Postgraduate Medicine, 107(2): 100-114, 2000.
Hay et al. "The Nature of Unexplained Chronic Aminotransferase Elevations of A Mild to Moderate Degree in Asymptomatic Patients", Hepatology, 9(2): 193-197, 1989.
Hayasaka et al. "Serum Markers as Tools to Monitor Liver Fibrosis", Digestion, 59: 381-384, 1998.
Henis et al. "Oligomeric Structure of the Human Asialoglycoprotein Receptor: Nature and Stoichiometry of Mutual Complexes Containing H1 and H2 Polypeptides Assessed by Fluorescence Photobleaching Recovery", The Journal of Cell Biology, XP007908595, 111(4): 1409-1418, Oct. 1990. p. 1410, r-h Col., § 2-3.
Kokudo et al. "Predictors of Successful Hepatic Resection: Prognostic Usefulness of Hepatic Asialoglycoprotein Receptor Analysis", Worl Journal of Surgery, XP007908592, 26(11): 1342-1347, Nov. 2002. Abstract.
Lederkremer et al. "An Alternatively Spliced Miniexon Alters the Subcellular Fate of the Human Asialglycoprotein Receptor H2 Subunit", The Journal of Biological Chemistry, 266(2): 1237-1244, 1991.
Moseley "Evaluation of Abnormal Liver Function Tests", Management of Chronic Liver Disease, 80(5): 887-906, 1996.
Tolchinsky et al. "Membrane-Bound Versus Secreted Forms of Human Asialglycoprotein Receptor Subunits", The Journal of Biological Chemistry, XP008101635, 271(24): 14496-14503, 1996.
Trojan et al. "Serum Tests for Diagnosis and Follow-Up of Hepatocellular Carcinoma After Treatment", Digestion, 59(Suppl.2): 72-74, 1998.
Wisdom "Enzyme-Immunoassay", Clinical Chemistry, 22(8): 1243-1255, 1976.
Yago et al "Detection and Quantification of Soluble Asialglycoprotein Receptor in Human Serum", Hepatology, XP000892931, 21(2): 383-388, Feb. 1, 1995.
Notice of Allowance Dated Jan. 15, 2010 From the US Patent and Trademark Office Re.: U.S. Appl. No. 11/224,148.
Response Dated Nov. 19, 2009 to Official Action of Aug. 21, 2009 From the US Patent and Trademark Office Re.: U.S. Appl. No. 11/224,148.
Translation of Office Action Dated Apr. 14, 2010 From the State Intellectual Property Office of the People's Republic of China Re. Application No. 200480013005.2.
Response Dated Jul. 21, 2010 to Office Action of Apr. 14, 2010 From the State Intellectual Property Office of the People's Republic of China Re. Application No. 200480013005.2.
Communication Pursuant to Article 94(3) EPC Dated Nov. 18, 2010 From the European Patent Office Re.: Application No. 04720548.9.

\* cited by examiner

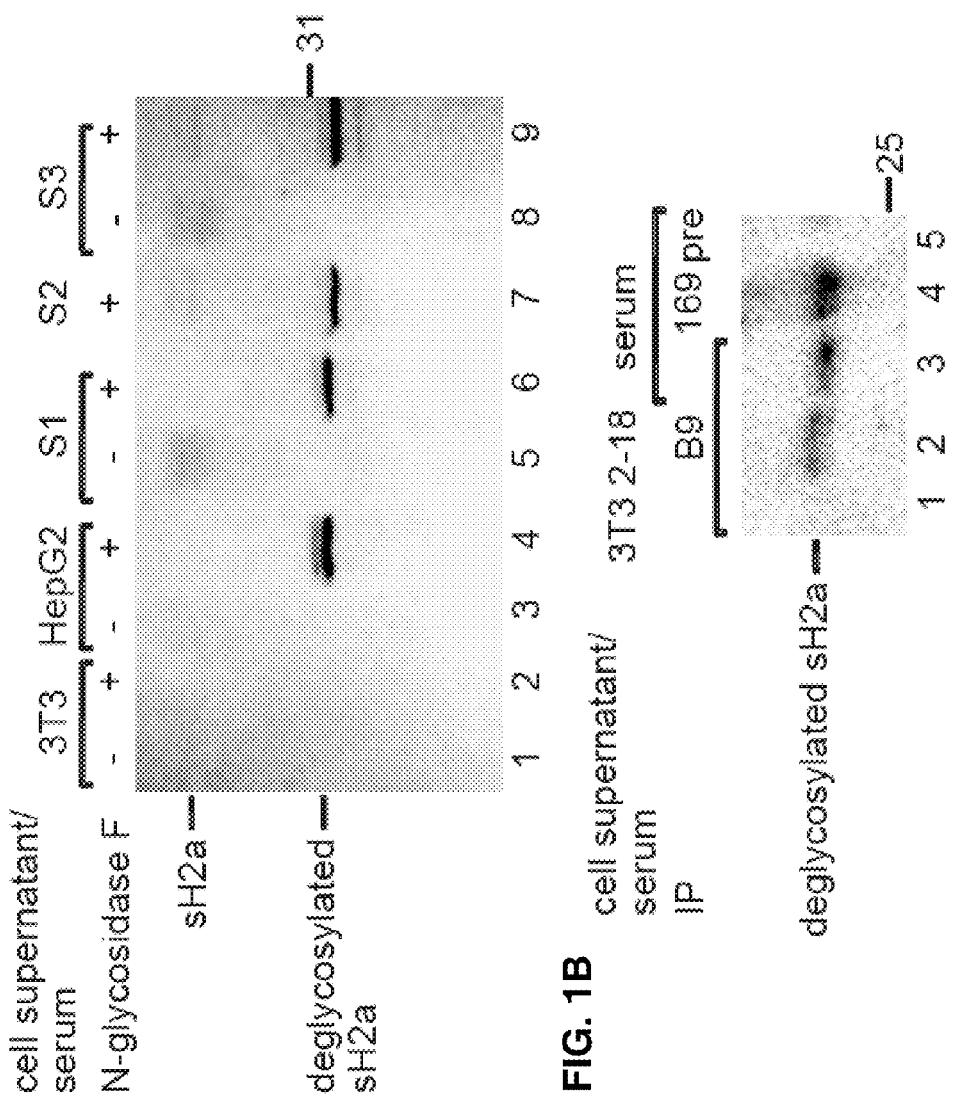

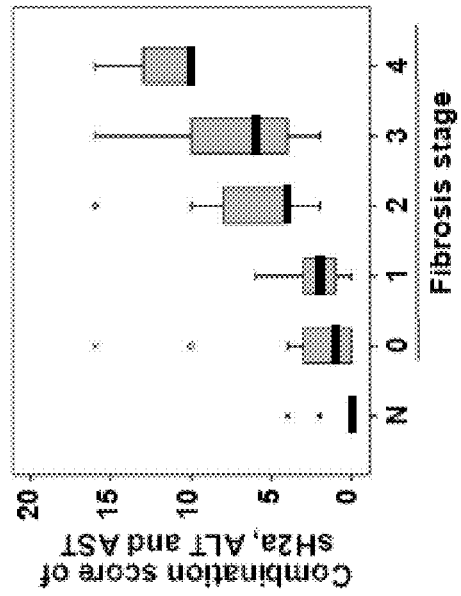
FIG. 2A
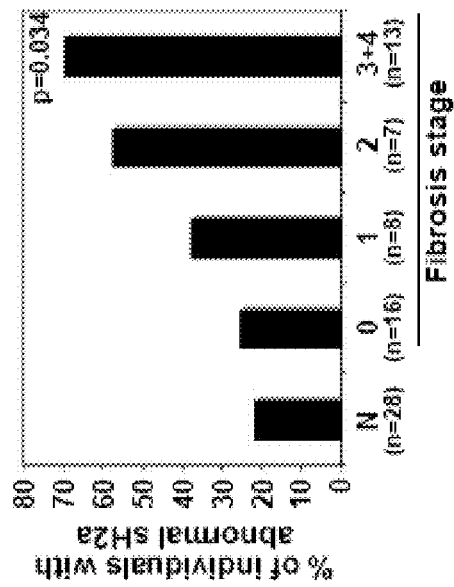
FIG. 2C
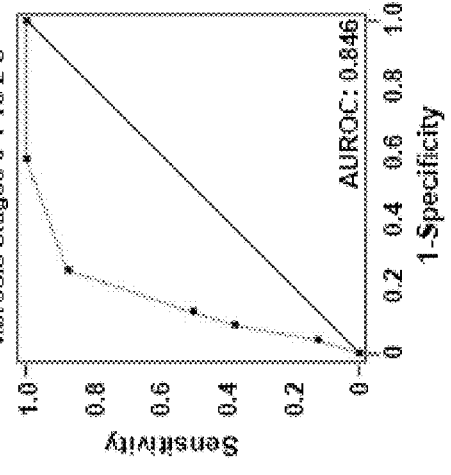
FIG. 2B sH2a score ROC for fibrosis stages 0-1 vs 3-4
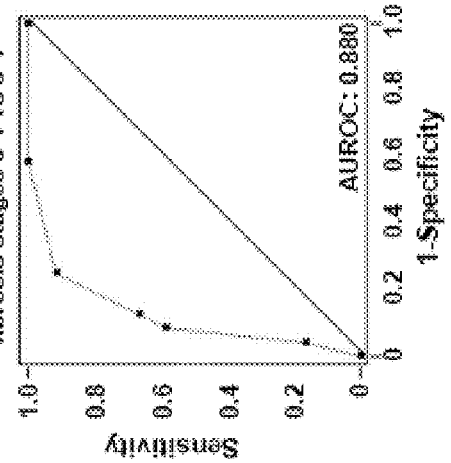
FIG. 2D combination score ROC for fibrosis stages 0-1 vs 3-4
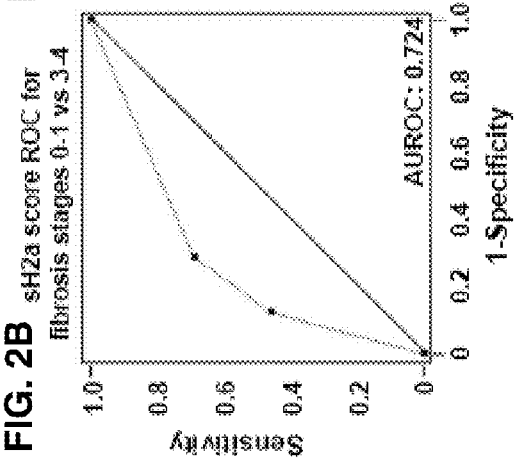
FIG. 2E combination score ROC for fibrosis stages 0-1 vs 2-3

METHODS FOR DIAGNOSING AND MONITORING LIVER DISEASES

RELATED APPLICATIONS

This application claims the benefit of priority of U.S. Provisional Patent Application No. 61/129,760, filed on Jul. 17, 2008, the contents of which are incorporated herein by reference.

BACKGROUND OF THE INVENTION

The present invention, in some embodiments thereof, relates to methods of diagnosing and monitoring liver diseases and, more particularly, but not exclusively, to liver fibrosis.

Soluble secreted proteins that are expressed uniquely in specific organs, or proteins whose formation or secretion is regulated by disease states, are excellent markers for disease. The reason for this is that the disease can be diagnosed by simply measuring the level of the secreted protein in serum of a potential patient. The level of a secreted protein in serum can be easily measured in a number of different ways that are well known in the art, such as ELISA assay and Western blotting, directed at quantifying marker levels in the serum sample. However, in order to have a good marker for a disease, the secreted protein must have distinctly different levels in normal and disease tissues. Furthermore, in order to provide accurate diagnoses in diseases that must be caught at early development stages in order to enable efficient treatment, such as cancer or fibrosis, the marker must have distinct expression or secretion levels even at an early stage of disease development.

Liver function can be affected by many chemicals, medicines, diet regimes, environmental poisons, alcohol abuse and viral infections that lead to hepatitis. The most common complications are liver fibrosis and cirrhosis. Generally, the origins of liver fibrosis that leads in its advanced stages to cirrhosis are common complications of Hepatitis B and C.

Hepatitis B is very common in Africa and in Asia, especially in the Philippines and in China and is endemic in the Middle East. In Europe and North America the incidence of known carriers is about 1 in a 1000 people. Worldwide, it is estimated that there are over 350 million hepatitis B (HBV) carriers, which represents 5% of the world's population. In addition it is estimated that 10 to 30 million people are infected with the hepatitis B virus each year. 10% of the people infected with HBV develop chronic infection. People with a chronic HBV infection are at risk of liver damage and around 20-30% of these people later develop cirrhosis.

Hepatitis C (HCV) is almost as common, and it is estimated that there are approximately 200 million people worldwide infected with the virus. There are up to 230,000 new HCV infections every year in the U.S. alone. Currently, 8,000 to 10,000 people infected with HCV die each year. Over the next 10-20 years, chronic HCV is predicted to become a major burden on the health care system, as patients who are currently asymptomatic with a relatively mild form of the disease, progress to end-stage liver disease and develop hepatocellular carcinoma. Progressive hepatic fibrosis and cirrhosis develop in 20% to 30% of patients with chronic HCV. There is no vaccine but liver fibrosis caused by this virus can be treated at early stages. Predictions in the USA indicate that there will be a 60% increase in the incidence of cirrhosis, a 68% increase in hepatoma incidence, a 279% increment in incidence of hepatic decompensation, a 528% increase in the need for transplantation, and a 223% increase in liver death rate. Altogether the number of fibrotic and cirrhotic patients worldwide in need of periodic diagnosis can be estimated at around 20 million, with up to 2 million added each year. With regard to the number of pre-fibrotic patients that would benefit from an early diagnosis, there could be several hundred million worldwide.

Generally, blood tests for liver function are based on the level of several markers such as alanine aminotransferase (ALT), aspartate aminotransferase (AST), alkaline phosphatase (ALP), gamma glutamic transpeptidase (GGT), bilirubin, albumin and prothrombin time (PT) in the serum. However, while the markers used in such "liver function tests" are capable of assessing hepatocyte integrity, which might be indicative of liver damage, most of them, except albumin and prothrombin, are not indicative of the synthesis function of the liver. Albumin, which is produced in the liver and circulates in the blood, is affected only when a liver disease is at a severe stage. On the other hand non-hepatic diseases such as nephrotic syndromes can affect albumin levels. Similarly, prothrombin, which is used to evaluate blood clotting disorders, is insensitive to mild liver disease and can be also affected by non-hepatic conditions such as dietary deficiencies or the use of anti-coagulants. Likewise, abnormal levels of bilirubin can result from hemolysis, ineffective erythropoiesis and other non-hepatic syndromes. In addition, as ALT, AST, ALP and GGT are also produced in organs other than the liver, their blood levels can be elevated in a wide range of non-hepatic diseases. Biochemical screening of healthy, asymptomatic people has revealed that up to 6% of the population exhibit abnormal levels of liver enzymes. However, the prevalence of liver disease in the general population is significantly lower (about 1%) (Gopal and Rosen, 2000, Postgraduate medicine; 107(2):100-2, 105-9, 113-4). Even though the current serum biochemical test pattern may suggest a specific diagnosis, confirmation usually requires further investigation using imaging studies and, possibly, liver biopsy.

Experimental serum markers that have been proposed for diagnosis of liver fibrosis include extracellular matrix (ECM) macromolecules and their degradation products such as N-terminal propeptide of type-III collagen (PIIINP), or the aminoterminal domain of procollagen type-IV (PIVNP), hyaluronic acid (HA), prolyl-hydroxylase, laminin, matrix metalloproteinase-1. The main problem with these markers is that they are not liver specific, not highly sensitive and can also reflect inflammation processes in other tissues. Recently, tests that combine several markers have been developed, for example Fibrotest (which includes α-2-macroglobulin, haptoglobin, apolipoprotein A1, GGT and total bilirubin). These and other combination tests provide a reasonable diagnosis for advanced fibrosis but are not satisfactory at low and intermediate fibrosis levels (Bissell 2004, Gastroenterology 2004; 127: 1847-49).

The only reliable and definitive test for liver function and status is a biopsy. However, biopsies cannot be used in standard tests, or for patients with mild conditions or even for routine periodic analysis in patients with severe liver disease. In addition, biopsy has only an 80% accuracy due to the small volume of tissue extracted and variations in the evaluation between pathologists (Poynard et al 2007, BMC Gastroenterol 2007; 7: 40).

The human asialoglycoprotein receptor (ASGPR) is expressed only in hepatocytes and serves in the clearance of asialoglycoproteins from the plasma (Drickamer, K., Cell, 1991. 67(6): p. 1029-1032). ASGPR levels are much lower in developing liver than in fully developed liver. The receptor level is also reduced in patients with cirrhosis and dramatically down-regulated in hepatocarcinomas (Doyle, D. B., Y and Petell, J, ed. The Liver: Biology and Pathobiology., ed. I. J. Arias, W B; Popper, H; Schachter, D and Shafritz, D A. 1988, Raven Press. 141).

The ASGPR is constructed of two subunits of related amino acid sequence, H1 (46 kD) and H2 (50 kD). H2a and H2b are two alternatively spliced variants of the ASGPR H2 subunit (Lederkremer, G. Z. and H. F. Lodish, J Biol Chem, 1991. 266(2): p. 1237-44). H2a differs from H2b only by the presence of an extra pentapeptide in the exoplasmic domain next to the membrane-spanning segment (Lederkremer, G. Z. and H. F. Lodish, J Biol Chem, 1991. 266(2): p. 1237-44). It was shown that H2a is rapidly cleaved next to this pentapeptide to a 35 kDa fragment, comprising the entire ectodomain, which is secreted, constituting a soluble form of the receptor (sH2a). Membrane-bound H2a does not participate in a receptor complex with H1 as is the case for H2b, and thus it is not a subunit of the receptor but a precursor for the soluble secreted form.

Although H2a is a type II transmembrane protein, indirect evidence suggests that signal peptidase is probably responsible for the cleavage to the soluble form. ASGPR sH2a was found to be efficiently secreted from the human hepatoma cell line HepG2. It was discovered that when H2a is expressed in stably transfected NIH 3T3 cells it is also cleaved, however only about 30% of sH2a can be Golgi processed and secreted from transfected fibroblasts and the rest is degraded at the ER (Tolchinsky, S. et al., J. Biol. Chem., 1996, 271(24): p. 14496-14503).

U.S. Application No. 20060286615 teaches diagnosing a liver condition by analyzing a level of sH2A in a sample of a subject.

SUMMARY OF THE INVENTION

According to an aspect of some embodiments of the present invention there is provided a method of diagnosing a liver disorder in a subject, the method comprising determining a level of sH2A and at least one additional liver marker in a sample of the subject wherein a change beyond a predetermined threshold in both the sH2A and the at least one additional marker with respect to a sample from a healthy individual is indicative of the liver disorder.

According to an aspect of some embodiments of the present invention there is provided a kit for diagnosing or monitoring a liver condition, comprising:
(i) a first agent capable of quantifying sH2A; and
(ii) a second agent capable of quantifying at least one additional liver marker.

According to some embodiments of the invention, the sample is selected from the group consisting of blood, urine and saliva.

According to some embodiments of the invention, the at least one additional liver marker is a soluble liver marker.

According to some embodiments of the invention, the soluble liver marker is selected from the group consisting of alanine aminotransferase (ALT), aspartate aminotransferase (AST), alkaline phosphatase (ALP), gamma glutamic transpeptidase (GGT), bilirubin, albumin and prothrombin (PT).

According to some embodiments of the invention, the soluble liver marker is alanine aminotransferase (ALT) and/or aspartate aminotransferase (AST).

According to some embodiments of the invention, a change in the alanine aminotransferase and/or the aspartate aminotransferase is an up-regulation.

According to some embodiments of the invention, a change in the sH2A is an up-regulation.

According to some embodiments of the invention, a change in the sH2A is a down-regulation.

According to some embodiments of the invention, the liver disease is selected from the group consisting of a hepatocellular carcinoma, a liver cirrhosis, a liver fibrosis and hepatitis.

According to some embodiments of the invention, the liver disease is liver fibrosis.

According to some embodiments of the invention, the method further comprises scoring the level of sH2A and the at least one additional liver marker.

According to some embodiments of the invention, a score of a normalized level of the sH2A is at least twice the score of a normalized level of an average of the at least one additional liver marker.

According to some embodiments of the invention, the diagnosing comprises staging the liver disease.

According to some embodiments of the invention, the at least one additional liver marker is alanine aminotransferase (ALT) and/or aspartate aminotransferase (AST).

According to some embodiments of the invention, a combination of the level of sH2A and the level of alanine aminotransferase (ALT) and the level of aspartate aminotransferase (AST) correlates with a stage of liver fibrosis.

According to some embodiments of the invention, the diagnosing is effected by:
(a) calculating an average of a normalized ALT level and a normalized AST level to obtain a normalized average ALT/AST value;
(b) indexing the normalized average ALT/AST value, wherein a normalized average value of less than 1.1 is equivalent to an index of 1, a normalized average value of 1.1-2 is equivalent to an index of 2 and a normalized average value greater than 2 is equivalent to an index of 3;
(c) calculating a normalized sH2A level to obtain a normalized sH2A value; and
(d) indexing the normalized sH2A value, wherein a normalized sH2A value of 0.85-1.19 is equivalent to an index of 2, a normalized sH2A value of 0.76-0.84 or 1.20-1.40 is equivalent to an index of 4 and a normalized sH2A value of less than 0.76 or greater than 1.46 is equivalent to an index of 6; and
(e) staging the liver fibrosis according to formula 1 [ALT/AST index×sH2A index]−2;
wherein a result of about 1 is indicative of a stage 0 of liver fibrosis;
a result of about 2 is indicative of a stage 1 of liver fibrosis;
a result of about 4 is indicative of a stage 2 of liver fibrosis;
a result of about 7 is indicative of a stage 3 of liver fibrosis; and
a result of about 11 is indicative of a stage 4 of liver fibrosis.

According to some embodiments of the invention, the first agent and the second agent are antibodies.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-B are photographs and graphs illustrating that sH2a is detected in normal human sera. FIG. 1A: Cell supernatants from 90 mm petri-dishes of NIH 3T3 (lanes 1-2) or HepG2 cells (lanes 3-4) or 0.3 ml of normal human sera from 3 donors (S1, lanes 5-6; S2, lane 7; S3, lanes 8-9) were immunoprecipitated with polyclonal anti-H2a carboxyterminal antibodies that were crosslinked to protein A-agarose, and the immunoprecipitates were subjected to 12% SDS-PAGE. Immunoblotting was then performed with anti-H2a carboxyterminal antibody followed by horseradish peroxidase-conjugated goat anti-rabbit IgG and color development with TMB. Samples on lanes 2, 4, 6, 7 and 9 were treated with N-glycosidase-F following immunoprecipitation. On the right is the molecular weight of a protein standard in kilodaltons. On the left are the migrations of sH2a prior to or following deglycosylation. FIG. 1B: Medium from two 90 mm dishes of control NIH 3T3 cells (lane 1) or of the same cells stably expressing sH2a (2-18 cell line, lane 2) or 0.5 ml of normal human serum (lanes 3-5) were immunoprecipitated with B9 monoclonal antibody (lanes 1-3), or with a mixture of polyclonal anti-H2a 169 and anti-carboxyterminal antibodies (lane 4) or with control preimmune rabbit serum (lane 5). All immunoprecipitates were treated with N-glycosidase-F and run on 12% SDS-PAGE followed by immunoblotting with anti-H2a carboxyterminal antibody and detection using the ECL procedure.

FIGS. 2A-E are graphs illustrating the correlation of sH2a and of the combination scores of sH2a, ALT and AST with fibrosis stage. FIG. 2A: The levels of sH2a in sera were compared between a group of 28 healthy individuals (N) and 44 HCV patients with different METAVIR fibrosis stages (0-4). Plotted is the percent of individuals in each group that showed abnormal sH2a levels (<0.85 or >=1.2× the level of a standard normal sample). In parenthesis are the numbers of individuals in each group. The p value is from Chi-square tests, comparing stages 3+4 to 0. FIG. 2B: ROC plot of sH2a scores for advanced fibrosis and cirrhosis (METAVIR 0-1 vs 3-4). FIG. 2C: The serum levels of sH2a, ALT and AST for each healthy individual (N) and for each HCV patient were joined in a combined score as detailed in the text. Patients were grouped by METAVIR fibrosis stage (0-4). In the boxplot the box height indicates the IQR in each group. The thick horizontal bar is the median. The whiskers extend to the farthest non-outlier value smaller than 1.5×IQR. Circles indicate "mild" outliers (<3×IQR) and asterisks show "extreme" outliers (>3×IQR). FIGS. 2D-E: ROC plots of the combined scores of sH2a, ALT and AST for advanced fibrosis and cirrhosis (METAVIR 0-1 vs 3-4) (FIG. 2D) or for intermediate and significant fibrosis (METAVIR 0-1 vs 2-3) (FIG. 2E).

DESCRIPTION OF PREFERRED EMBODIMENTS

Figure 3:
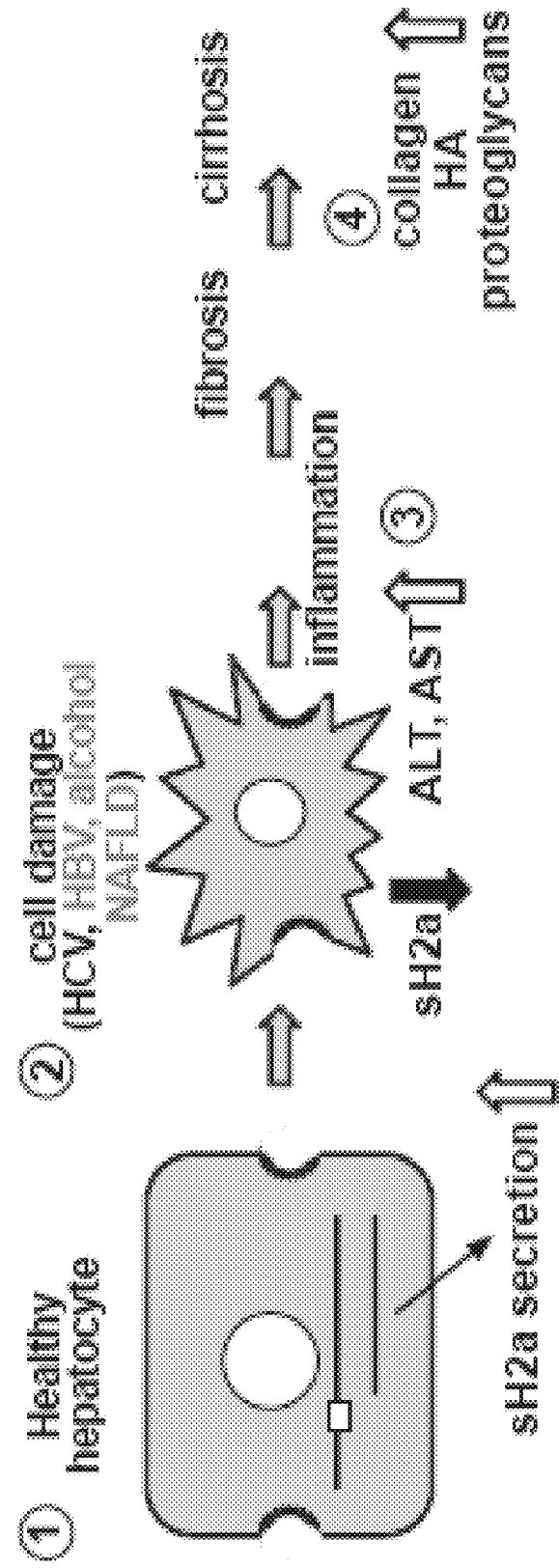
FIG. 3 is a model depicting the sequence of events in the fibrogenic process and changes in ASGPR sH2a secretion. The membrane-bound precursor of sH2a is cleaved in the endoplasmic reticulum of healthy hepatocytes, traverses the secretory pathway and is secreted to the plasma (step 1). As a consequence of HCV infection and possibly following other insults, hepatocytes are damaged, their overall function is compromised and sH2a secretion is reduced, while intracellular enzymes like ALT and AST are released to the plasma (step 2). This starts a process of inflammation (step 3), activation of hepatic stellate cells leading to fibrosis and then cirrhosis, which involve secretion and progressive accumulation of ECM components (step 4).

The present invention, in some embodiments thereof, relates to methods of diagnosing and monitoring liver diseases and, more particularly, but not exclusively, to liver fibrosis.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The human asialoglycoprotein receptor is a membrane heterooligomer expressed exclusively in hepatocytes. A soluble secreted form, sH2a, arises, not by shedding at the cell surface, but by intracellular cleavage of its membrane-bound precursor, which is encoded by an alternatively spliced form of the receptor H2 subunit. sH2a is known to be present at constant levels in serum from healthy individuals but is altered in patients with distorted liver function.

In order to obtain a more accurate diagnostic test for liver function, the present inventor investigated the predictive power of measuring sH2A (a marker of liver function) together with measurement of additional markers that are predictive of liver damage. The present inventor postulated that function and damage markers may give complementary information and when combined may provide a more accurate diagnostic test.

While reducing the present invention to practice, the present inventor showed that measurement of sH2A together with ALT and AST provided an accurate prediction of the fibrosis stage, including early and intermediate stages of fibrosis that other markers fail to detect (FIGS. 2C-E).

Thus, according to one aspect of the present invention there is provided a method of diagnosing a liver disorder in a subject, the method comprising determining a level of sH2A and at least one additional liver marker in a sample of the subject wherein a change beyond a predetermined threshold in both the sH2A and the at least one additional marker with respect to a sample from a healthy individual is indicative of the liver disorder.

As used herein the term "diagnosing" refers to classifying a liver disorder, determining a severity of a liver disorder (grade or stage), monitoring the liver disorder progression, forecasting an outcome of the liver disorder and/or prospects of recovery, monitoring of the outcome of treatment and monitoring the success of liver transplant.

The subject may be a healthy human subject undergoing a routine well-being check up, or may have been previously diagnosed with the liver disorder. Alternatively, the subject may be at risk of having the liver disorder (e.g., a genetically predisposed subject, a subject with medical and/or family history of cancer, a subject who has been exposed to carcinogens, occupational hazard, environmental hazard, alcoholic, obese, infected with HBV or HCV], and/or a subject who exhibits suspicious clinical signs of a liver disorder.

In one embodiment, the methods of the invention are useful for differentiating individuals having a Metavir score of F0 or F1 from individuals having a Metavir score of F2, F3 or F4. Metavir scoring is a well accepted system for grading liver biopsy specimens and is described in Knodell (Hepatology 1:431-435 (1981). F0 is equivalent to the absence of fibrosis; F1 signifies portal fibrosis without septa. F2 signifies portal fibrosis with a few septa. F3 signifies numerous septa without cirrhosis. F4 signifies cirrhosis.

The liver disease which is detected or monitored can be can be in a chronic or active state. Exemplary liver diseases include, but are not limited to liver fibrosis, hepatocellular carcinoma, liver cirrhosis and hepatitis.

The phrase "liver fibrosis" refers to the growth of scar tissue in the liver due to any of a variety of chronic toxic insults, including, but not limited to, chronic alcohol abuse; chronic exposure to drugs (e.g., acetominophen, amiodarone, aspirin, azathioprine, isoniazid, methyldopa, methotrexate, mitrfurantoin, propylthiouracil, and sulfonamides); chronic exposure to certain chemical agents (e.g., carbon tetrachloride, dimethyl nitrosamine, vinyl chloride, polychlorinated biphenyls, aflatoxins, and pesticides); infection with *Schistosoma mansoni*; infection with HBV; infection with HCV; diabetes; autoimmune disorders (e.g., primary sclerosing cholangitis, primary biliary cirrhosis, autoimmune hepatitis, lupoid hepatitis), and inflammatory bowel disease; hemochromatosis; alpha-1-antitrysin deficiency; chronic cholestatic hepatitis; non-alcoholic steatohepatitis; chronic biliary obstruction; Wilson's disease; and other conditions known to cause cirrhosis.

Liver cirrhosis is a degenerative condition in which the liver parenchyma deteriorates, the lobules are infiltrated with fat and dense perilobular connective tissues are formed. As a result, the blood supply to the remaining cells is reduced leading to portal hypertension and eventually death.

As described above, fibrosis and cirrhosis can result from several situations, including but not limited to alcohol abuse, poisoning, food poisoning, side effects of medical treatments such as treatment with cholesterol lowering drugs like statins, drug abuse, side effects of drug combination, drugs that metabolize into liver damaging agents, side effects of exposure to chemicals such as in a work place, at time of war or in a terrorist act, hepatitis including viral hepatitis, a bacterial or protozoal infection, and liver failure, including acute and fulminant hepatic failure for example. Examples of statins include but are not limited to, simvastatin, lovastatin, mevastatin, pravastatin, fluvastatin, atorvastatin, cerivastatin, and pitavastatin. However, it should be noted that other drugs and/or drug combinations may also cause liver damage, fibrosis and/or cirrhosis.

Due to the many possible causes for liver cancer, fibrosis and cirrhosis, many people are in danger of developing these diseases, and should be tested for early detection or monitoring of the diseases. People in danger of developing liver disease include, but are not limited to Hepatitis B or C positives, HIV positives, bacterial or protozoal hepatitis carriers, patients receiving potential liver-damaging anesthetics, patients taking medicines with potential liver-damaging effects (e.g. cholesterol-lowering drugs such as statins), cancer patients with tumors in other organs, alcoholics and wine tasters, employees working with liver-damaging agents, victims of biological or chemical attacks in war or terrorist acts and victims of poisoning or food poisoning, as well as patients who may be particularly sensitive to drugs having effects on the liver, including but not limited to, the elderly and children (both of whom have lower metabolic capabilities for metabolizing drugs in the liver), and/or patients with reduced liver function, and/or patients receiving multiple drug treatments which may interact in terms of liver metabolism, particularly in patients who are already at some risk (such as those patients in the previous categories for example). The antibodies, methods, kits and assays taught in the present invention may be used for monitoring the condition of all the aforementioned individuals.

In addition, there are some genetic diseases, such as Wilson's disease, HHC, and alpha-1 AntiTrypsin deficiency ($\alpha$-1AT), that cause the liver to dysfunction, and may cause cirrhosis or chronic hepatitis. As of yet, no single test may be used to diagnose or monitor the development of Wilson's disease. The present invention may be used to monitor patients carrying mutations for this disease, and may possibly also be used for prenatal genetic testing and diagnosis, and may also be used in gene therapy. Therefore, according to a further preferred embodiment of the present invention, monitoring or diagnosing liver disease in a subject preferably includes monitoring and diagnosing liver disease caused by a genetic mutation. Optionally and preferably, the subject may be a fetus, when using the method as a diagnostic tool in prenatal genetic testing.

A variety of samples can be useful in practicing the methods of the invention including, for example, fluid samples such as blood, serum, plasma, urine, saliva and solid samples such as liver tissue. In one embodiment, a single sample is obtained from the individual to be diagnosed. Such a sample can be, for example, a serum sample.

The sample can be, for example, a fluid sample such as whole blood, plasma, saliva, urine, synovial fluid or other bodily fluid, or a tissue sample such as a liver tissue sample. One skilled in the art understands that fluid samples can be diluted, if desired, prior to analysis.

As mentioned, the diagnostic method of the present invention comprises detecting changes in the level of sH2A and at least one additional liver marker.

As used herein, the term "sH2A" refers to a soluble secreted form of the human asialoglycoprotein receptor (AS-GPR). sH2a arises by juxtamembrane cleavage from the precursor membrane bound H2A polypeptide. According to one embodiment the sH2A has an amino acid sequence as set forth in SEQ ID NO: 2 and GenBank No. EAW90263.1.

As used herein, the phrase "determining a level of sH2A" refers to any direct or indirect quantitative assay for sH2A.

The phrase "at least one additional liver marker" refers to a biomolecule whose amount correlates with liver function or liver damage. It is understood that determining a level of at least one additional liver marker may be performed simultaneously with determining a level of sH2A or in any order and using any combination of assay formats. The value of the level can be obtained from a secondary source, such as a physician or diagnostic laboratory or can be determined using any convenient sample and assay, including but not limited to those described herein below.

Suitable biomolecules which may be detected include, but are not limited to, polypeptides, polynucleotides (e.g. miR-NAs), lipids, carbohydrates and steroids. Exemplary polypeptides that may be detected include enzymes, antibodies; antigens; cellular membrane antigens and receptors (neural, hormonal, nutrient, and cell surface receptors) or their ligands.

Exemplary additional liver markers include, without limitation, collagens such as collagen type I; fibronectin; vitronectin; endothelin; undulin; adhesion molecules such as selectins, vascular cell adhesion molecules (VCAMs) and intercellular adhesion molecules (ICAMs); pro-inflammatory cytokines such as tumor necrosis factor-alpha (TNF-alpha); pseudocholinesterase; manganese superoxide dismutase; N-acetyl-beta-glucosaminidase (beta-NAG); glutathione peroxidase; connective tissue growth factor (CTGF); platelet derived growth factor (PDGF); PDGF receptor; monocyte chemotactic protein-1 (MCP-1); inducible nitric oxide synthetase; nitrotyrosine; bilirubin; ferritin and alpha-fetoprotein; gamma-glutamyl transpeptidase (GGT); aspartate aminotransferase (AST); alanine aminotransferase (ALT); alpha2-MG, TIMP-1 bilirubin, ferritin, retinol binding protein 4 (RBP4), hyaluronic acid (HA), antithrombin III, sorbital dehydrogenase (SDH), lactate dehydrogenase (LDH), alpha-glutathione S-transferase and prothrombin (PT).AST/ALT ratio; albumin; gamma-globulins; betagamma-block; prothrombin index; Child-Pugh score; PGA index (prothrombin time, GGT concentration and apoA1 concentration); PGAA index (PGA score with alpha2-macroglobulin level); hemoglobin; mean corpuscular volume; lymphocyte count; cholesterol; urea; creatinine; sodium and platelet count.

According to one embodiment, the marker is secreted (i.e. soluble).

Methods of detecting changes in amounts of polypeptide markers are typically affected with antibodies—either monoclonal or polyclonal.

The term "antibody" as used to describe this invention includes intact molecules as well as functional fragments thereof, such as Fab, F(ab')$_2$, Fv and scFv that are capable of specific, high affinity binding to a human major histocompatibility complex (MHC) class I complexed with a HLA-restricted antigen. These functional antibody fragments are defined as follows:

(i) Fab, the fragment which contains a monovalent antigen-binding fragment of an antibody molecule, can be produced by digestion of whole antibody with the enzyme papain to yield an intact light chain and a portion of one heavy chain;

(ii) Fab', the fragment of an antibody molecule that can be obtained by treating whole antibody with pepsin, followed by reduction, to yield an intact light chain and a portion of the heavy chain; two Fab' fragments are obtained per antibody molecule;

(iii) F(ab')$_2$, the fragment of the antibody that can be obtained by treating whole antibody with the enzyme pepsin without subsequent reduction; F(ab')$_2$ is a dimer of two Fab' fragments held together by two disulfide bonds;

(iv) Fv, defined as a genetically engineered fragment containing the variable region of the light chain and the variable region of the heavy chain expressed as two chains; and (v) scFv or "single chain antibody" ("SCA"), a genetically engineered molecule containing the variable region of the light chain and the variable region of the heavy chain, linked by a suitable polypeptide linker as a genetically fused single chain molecule.

Methods of making these fragments are known in the art. See for example, Harlow and Lane, Antibodies: A Laboratory Manual, Cold Spring Harbor Laboratory, New York, 1988, incorporated herein by reference.

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of V$_H$ and V$_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise V$_H$ and V$_L$ chains connected by a peptide linker. These single-chain antigen binding proteins (sFv) are prepared by constructing a structural gene comprising DNA sequences encoding the V$_H$ and V$_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

U.S. Application No. 20060286615 incorporated herein by reference teaches monoclonal antibodies capable of detecting sH2A and a hybridoma cell line capable of producing same. In addition, the Examples section herein below describes generation of a monoclonal antibody capable of detecting sH2A. Antibodies for detecting additional liver markers are also known in the art. For example antibodies for detecting ALT and AST are used routinely in liver function tests and are widely commercially available.

Exemplary methods of detecting polypeptide markers of the present invention are summarized below:

Enzyme linked immunosorbent assay (ELISA): This method involves fixation of a sample containing a protein substrate to a surface such as a well of a microtiter plate. A substrate specific antibody coupled to an enzyme is applied and allowed to bind to the substrate. Presence of the antibody is then detected and quantitated by a calorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, calorimetric reaction or chemiluminescence. This method allows both quantitation of an amount of substrate and determination of its identity by a relative position on the membrane which is indicative of a migration distance in the acrylamide gel during electrophoresis.

Radio-immunoassay (RIA): In one version, this method involves precipitation of the desired protein (i.e., the substrate) with a specific antibody and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

In vitro activity assays: In these methods the activity of a particular enzyme is measured in a protein mixture extracted from the cells. The activity can be measured in a spectrophotometer well using colorimetric methods or can be measured in a non-denaturing acrylamide gel (i.e., activity gel). Following electrophoresis the gel is soaked in a solution containing a substrate and calorimetric reagents. The resulting stained band corresponds to the enzymatic activity of the protein of interest. If well calibrated and within the linear range of response, the amount of enzyme present in the sample is proportional to the amount of color produced. An enzyme standard is generally employed to improve quantitative accuracy.

It will be appreciated that polypeptide markers may also be detected at the polynucleotide level.

Exemplary methods of detecting levels of polynucleotides are listed herein below.

Northern Blot analysis: This method involves the detection of a particular RNA in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radio-isotopes or enzyme linked nucleotides. Detection may be using autoradiography, colorimetric reaction or chemiluminescence. This method allows both quantitation of an amount of particular RNA molecules and determination of its identity by a relative position on the membrane which is indicative of a migration distance in the gel during electrophoresis.

RT-PCR analysis: This method uses PCR amplification of relatively rare RNAs molecules. First, RNA molecules are purified from the cells and converted into complementary DNA (cDNA) using a reverse transcriptase enzyme (such as an MMLV-RT) and primers such as, oligo dT, random hexamers or gene specific primers. Then by applying gene specific primers and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules. It will be appreciated that a semi-quantitative RT-PCR reaction can be employed by adjusting the number of PCR cycles and comparing the amplification product to known controls.

RNA in situ hybridization stain: In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the slide is subjected to either a photographic emulsion which reveals signals generated using radio-labeled probes or to a colorimetric reaction which reveals signals generated using enzyme-linked labeled probes.

In situ RT-PCR stain: This method is described in Nuovo G J, et al. [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

DNA Microarrays/DNA Chips:

The expression of thousands of genes may be analyzed simultaneously using DNA microarrays, allowing analysis of the complete transcriptional program of an organism during specific developmental processes or physiological responses. DNA microarrays consist of thousands of individual gene sequences attached to closely packed areas on the surface of a support such as a glass microscope slide. Various methods have been developed for preparing DNA microarrays. In one method, an approximately 1 kilobase segment of the coding region of each gene for analysis is individually PCR amplified. A robotic apparatus is employed to apply each amplified DNA sample to closely spaced zones on the surface of a glass microscope slide, which is subsequently processed by thermal and chemical treatment to bind the DNA sequences to the surface of the support and denature them. Typically, such arrays are about 2×2 cm and contain about individual nucleic acids 6000 spots. In a variant of the technique, multiple DNA oligonucleotides, usually 20 nucleotides in length, are synthesized from an initial nucleotide that is covalently bound to the surface of a support, such that tens of thousands of identical oligonucleotides are synthesized in a small square zone on the surface of the support. Multiple oligonucleotide sequences from a single gene are synthesized in neighboring regions of the slide for analysis of expression of that gene. Hence, thousands of genes can be represented on one glass slide. Such arrays of synthetic oligonucleotides may be referred to in the art as "DNA chips", as opposed to "DNA microarrays", as described above [Lodish et al. (eds.). Chapter 7.8: DNA Microarrays: Analyzing Genome-Wide Expression. In: Molecular Cell Biology, 4th ed., W.H. Freeman, New York. (2000)].

Oligonucleotide microarray—In this method oligonucleotide probes capable of specifically hybridizing with the polynucleotides of the present invention are attached to a solid surface (e.g., a glass wafer). Each oligonucleotide probe is of approximately 20-25 nucleic acids in length. To detect the expression pattern of the polynucleotides of the present invention in a specific cell sample (e.g., blood cells), RNA is extracted from the cell sample using methods known in the art (using e.g., a TRIZOL solution, Gibco BRL, USA). Hybridization can take place using either labeled oligonucleotide probes (e.g., 5'-biotinylated probes) or labeled fragments of complementary DNA (cDNA) or RNA (cRNA). Briefly, double stranded cDNA is prepared from the RNA using reverse transcriptase (RT) (e.g., Superscript II RT), DNA ligase and DNA polymerase I, all according to manufacturer's instructions (Invitrogen Life Technologies, Frederick, Md., USA). To prepare labeled cRNA, the double stranded cDNA is subjected to an in vitro transcription reaction in the presence of biotinylated nucleotides using e.g., the BioArray High Yield RNA Transcript Labeling Kit (Enzo, Diagnostics, Affymetix Santa Clara Calif.). For efficient hybridization the labeled cRNA can be fragmented by incubating the RNA in 40 mM Tris Acetate (pH 8.1), 100 mM potassium acetate and 30 mM magnesium acetate for 35 minutes at 94° C. Following hybridization, the microarray is washed and the hybridization signal is scanned using a confocal laser fluorescence scanner which measures fluorescence intensity emitted by the labeled cRNA bound to the probe arrays.

For example, in the Affymetrix microarray (Affymetrix®, Santa Clara, Calif.) each gene on the array is represented by a series of different oligonucleotide probes, of which, each probe pair consists of a perfect match oligonucleotide and a mismatch oligonucleotide. While the perfect match probe has a sequence exactly complimentary to the particular gene, thus enabling the measurement of the level of expression of the particular gene, the mismatch probe differs from the perfect match probe by a single base substitution at the center base position. The hybridization signal is scanned using the Agilent scanner, and the Microarray Suite software subtracts the non-specific signal resulting from the mismatch probe from the signal resulting from the perfect match probe.

Below is a description of typical methods used to detect specific liver markers:

Assays for detection of biochemical or serological markers useful in the invention are well known in the art and in many cases commercially available. Assays for PIIINP, laminin, tenascin, collagen type IV, collagen type VI, YKL-40, MMP-3, MMP-2, MMP-9/TIMP-1 complex, sFas ligand, TGF-beta1, IL-10, apoA1, apoA2 and apoB are commercially available from various sources as summarized in Table 1.

TABLE 1

| Marker | Company | Assay | Catalog number |
| --- | --- | --- | --- |
| PIIINP | Orion Diagnostica, ESPO, Finland | RIA | 05903 |
| Laminin | Chemicon Intl. (Temecula, CA) | ELISA | ECN310 |
| Tenascin | Chemicon Intl. (Temecula, CA) | ELISA | ECM320 |
| Collagen IV | Iatron Laboratories (Tokyo, Japan) | RIA | KCAD1 |
| YKL-40 | Metra Biosystems (Mountain View, CA) | ELISA | 8020 |
| MMP-3 | Amersham Pharmacia (Piscataway, NJ) | ELISA | RPN2613 |

TABLE 1-continued

| Marker | Company | Assay | Catalog number |
| --- | --- | --- | --- |
| MMP-2 | Amersham Pharmacia (Piscataway, NJ) | ELISA | RPN2617 |
| MMP-9/TIMP-1 complex | SBA Sciences (Turku, Finland) | ELISA | MP2215 |
| sFas ligand | Bender MedSystems Diagnostics (Vienna, Austria) | ELISA | BMS260/2 |
| TGF-B1 | R&D Systems (Minneapolis, MN) | ELISA | DB100 |
| IL-10 | R&D Systems (Minneapolis, MN) | ELISA | HS100B |
| apoA1 | AlerChek, Inc. (Portland, ME) | ELISA | A70101 |
| apoA2 | AlerChek, Inc. (Portland, ME) | ELISA | A70102 |
| apoB | Sigma Diagnostics (St. Louis, MO) | IT - immunoturbidimetric | 357-A |

Methods of detecting alpha2-macroglublin, hyaluronic acid and tissue inhibitor of a metalloproteinase-1 (TIMP-1) are disclosed in US Patent Application 20060084057, incorporated herein by reference.

Fibronectin can be conveniently assayed by turbidimetric assay available from Roche Diagnostics (Mannheim, Germany). Pseudocholinesterase (PCHE) can be assayed using standard methodology available from Boehringer. Levels of N-acetyl-beta-glucosaminidase (beta-NAG) can be determined by assaying for enzymatic activity using a kit available from Cortecs diagnostics. Manganese superoxide dismutase (Mn-SOD) levels can be conveniently determined by ELISA using a kit available, for example, from Bender MedSystem. Glutathione peroxidase levels can be determined by assaying for enzymatic activity using, for example, a kit available from Randox Laboratories Ltd (Oceanside, Calif.).

Total or direct bilirubin, GGT, AST and ALT levels can be determined using an autoanalyser such as Hitachi 917 Automate (Mannheim, Germany) with Roche Diagnostics reagents. Albumin levels can be determined, for example, by the bromocresol green method as described in Doumas et al., Clin. Chim Acta 31:87-96 (1971); and ferritin and alpha-fetoprotein levels can be conveniently determined using, for example, an immunoassay available from Boehringer. In addition, levels of alpha, globulin, $alpha_2$ globulin, beta globulin and gamma-globulin can be determined, for example, by serum protein electrophoresis in an automatic system (Hydrasys and Hyrys, Sebia; Issy-Les-Moulineaux, France). Methods of determining prothrombin activity also are well known in the art and include the clotting method available from Organon Technika (West Orange, N.J.). PGA index can be determined as described in Poynard et al., Gastroenterol. 100:1397-1402 (1991), and PGAA index also can be determined by well known methods as described in Naveau et al., Dig. Dis. Sci. 39:2426-2432 (1994)).

Platelet counts, lymphocyte counts, mean corpuscular volume and related variables can be determined by a variety of methodologies using, for example, a Bayer-Technicon H2 analyser (Bayer-Technicon Instruments; Tarrytown, N.Y.). Cholesterol levels can be determined by standard methodologies available, for example, from Boehringer. Thus, it is clear to the skilled person that a variety of methodologies, including but not limited to the above, are well known in the art and can be useful in the diagnostic methods of the invention.

The agents capable of quantifying sH2A may be packaged together with agents capable of quantifying the additional markers of the present invention in a pack such as a FDA approved kit. The pack may, for example, comprise metal or plastic foil, such as a blister pack. The pack or dispenser device may be accompanied by instructions for diagnosis. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Diagnosis is based on analyzing the sample for a level of sH2A and the additional liver marker and comparing them to reference values (i.e. the predetermined level), where the reference values serve to assist in differentiating those with a liver disorder from other individuals.

The present inventors have shown that either an up-regulation or a down-regulation of sH2A compared to an amount in a healthy subject is indicative of abnormal liver function.

It will be appreciated that the level of sH2A and additional liver markers may be reported in absolute terms or may be scored. According to one embodiment, a score of a normalized level of sH2A is at least twice the score of a normalized level of an average of the at least one additional liver marker.

According to an exemplary embodiment of this aspect of the present invention the levels of alanine aminotransferase (ALT) and/or aspartate aminotransferase (AST) are used to diagnose a liver disease in combination with sH2A. Typically, an upregulation of either of these enzymes is indicative of a liver disease.

The present inventors have shown that analyzing the levels of sH2A, ALT and AST allows for staging of a liver disease.

An exemplary method for staging a liver fibrosis is set forth herein below:

1. calculate an average of a normalized ALT level and a normalized AST level to obtain a normalized average ALT/AST value;

2. index the normalized average ALT/AST value, wherein a normalized average value of less than 1.1 is equivalent to an index of 1, a normalized average value of 1.1-2 is equivalent to an index of 2 and a normalized average value greater than 2 is equivalent to an index of 3;

3. calculate a normalized sH2A level to obtain a normalized sH2A value; and 4. index the normalized sH2A value, wherein a normalized sH2A value of 0.85-1.19 is equivalent to an index of 2, a normalized sH2A value of 0.76-0.84 or 1.20-1.40 is equivalent to an index of 4 and a normalized sH2A value of less than 0.76 or greater than 1.46 is equivalent to an index of 6; and 5. stage the liver fibrosis according to formula 1 [ALT/AST index×sH2A index]−2;

wherein a result of about 1 is indicative of a stage 0 of liver fibrosis;

a result of about 2 is indicative of a stage 1 of liver fibrosis;
a result of about 4 is indicative of a stage 2 of liver fibrosis;
a result of about 7 is indicative of a stage 3 of liver fibrosis; and
a result of about 11 is indicative of a stage 4 of liver fibrosis.

It will be appreciated that steps 1-4 can be performed simultaneously or in reverse order (i.e. first find sH2A values and then ALT and AST values.

Additional algorithms may be generated to further improve the sensitivity and specificity of the assays of the present invention. The precise algorithm will depend on the markers selected and the weight each contributes to the predictive value of the disease. The algorithms are typically formulated using true positives, false positives, true negatives and false negatives. A "true positive" sample is a sample positive for the indicated stage of fibrosis according to clinical biopsy, which is also diagnosed positive according to a method of the invention. A "false positive" sample is a sample negative for the indicated stage of fibrosis by biopsy, which is diagnosed positive according to a method of the invention. Similarly, a "false negative" is a sample positive for the indicated stage of fibrosis by biopsy, which is diagnosed negative according to a method of the invention. A "true negative" is a sample negative for the indicated stage of fibrosis by biopsy, and also negative for fibrosis according to a method of the invention. See, for example, Motulsky (Ed.), Intuitive Biostatistics New York: Oxford University Press (1995).

As used herein, the term "sensitivity" means the probability that a diagnostic method of the invention gives a positive result when the sample is positive. Sensitivity is calculated as the number of true positive results divided by the sum of the true positives and false negatives. Sensitivity essentially is a measure of how well a method correctly identifies those with fibrotic disease. In a method of the invention, the weights of each liver marker can be selected such that the sensitivity of diagnosing an individual is at least about 70%, and can be, for example, at least 75%, 80%, 85%, 90% or 95% in at least 60% of the patient population assayed, or in at least 65%, 70%, 75% or 80% of the patient population assayed.

As used herein, the term "specificity" means the probability that a diagnostic method of the invention gives a negative result when the sample is not positive. Specificity is calculated as the number of true negative results divided by the sum of the true negatives and false positives. Specificity essentially is a measure of how well a method excludes those who do not have fibrosis. In a method of the invention, the weights of each liver marker can be selected such that when the sensitivity is at least about 70%, the specificity of diagnosing an individual is in the range of 70-100%, for example, at least 75%, 80%, 85%, 90% or 95% in at least 60% of the patient population assayed, or in at least 65%, 70%, 75% or 80% of the patient population assayed.

The term "negative predictive value," as used herein, is synonymous with "NPV" and means the probability that an individual diagnosed as not having fibrosis actually does not have the disease. Negative predictive value can be calculated as the number of true negatives divided by the sum of the true negatives and false negatives. Negative predictive value is determined by the characteristics of the diagnostic method as well as the prevalence of fibrosis in the population analyzed. In a method of the invention, the weights of each liver marker can be selected such that the negative predictive value in a population having a liver fibrosis prevalence of up to 10% is in the range of 75-99% and can be, for example, at least 80%, at least 85%, at least 90%, or at least 95%, in at least 60% of the patient population assayed, for example, in at least 65%, 70%, 75% or 80% of the patient population assayed. The weights of each liver marker can also be selected such that the negative predictive value in a population having a liver fibrosis prevalence of up to 20% is in the range of 75-99% and can be, for example, at least 80%, at least 85%, at least 90%, or at least 95%, in at least 60% of the patient population assayed, for example, in at least 65%, 70%, 75% or 80% of the patient population assayed. In addition, the weights of each liver marker can be selected such that the negative predictive value in a population having a liver fibrosis prevalence of up to 30% is in the range of 75-99% and can be, for example, at least 80%, at least 85%, at least 90%, or at least 95%, in at least 60% of the patient population assayed, for example, in at least 65%, 70%, 75% or 80% of the patient population assayed.

The term "positive predictive value," as used herein, is synonymous with "PPV" and means the probability that an individual diagnosed as having fibrosis actually has the condition. Positive predictive value can be calculated as the number of true positives divided by the sum of the true positives and false positives. Positive predictive value is determined by the characteristics of the diagnostic method as well as the prevalence of fibrosis in the population analyzed. In a method of the invention, the weights of each liver marker can be selected such that, in a patient population having up to 10% liver fibrosis prevalence, the positive predictive value of the method is at least about 75%, and can be at least 80%, at least 85%, at least 90% or at least 95% in at least 60% of the patient population assayed, for example, in at least 65%, 70%, 75% or 80% of the patient population assayed. The weights of each liver marker can also be selected such that, in a patient population having up to 20% liver fibrosis prevalence, the positive predictive value of the method is at least about 75%, and can be at least 80%, at least 85%; at least 90% or at least 95% in at least 60% of the patient population assayed, for example, in at least 65%, 70%, 75% or 80% of the patient population assayed. Similarly, the weights of each liver marker can be selected such that in a patient population having up to 30% liver fibrosis prevalence, the positive predictive value of the method is at least about 75%, and can be at least 80%, at least 85%, at least 90% or at least 95% in at least 60% of the patient population assayed, for example, in at least 65%, 70%, 75% or 80% of the patient population assayed.

Predictive values, including negative and positive predictive values, are influenced by the prevalence of the disease in the population analyzed. In the methods of the invention, the weights of each liver marker can be selected such that can be selected to produce a desired clinical parameter for a clinical population with a particular liver fibrosis prevalence. For example, weights can be selected for a liver fibrosis prevalence of up to 10%, 12%, 15%, 18%, 20%, 25% or 30% which can be seen, for example, in a hepatologist's office. Cut-off values also can be selected for a liver fibrosis prevalence of up to 1%, 2%, 3%, 4%, 5%, 6%, 7% or 8%, which can be representative of the fibrosis prevalence seen in a general practitioner's office.

As used herein, the term "accuracy" means the overall agreement between the diagnostic method and the disease state. Accuracy is calculated as the sum of the true positives and true negatives divided by the total number of sample results, and is affected by the prevalence of fibrosis in the population analyzed. The weights of each liver marker can be selected such that the accuracy of a method of the invention in a patient population having a liver fibrosis prevalence of up to 10% is at least about 80% and can be, for example, at least 85%, 90%, 91%, 92%, 93%, 94%, 95%, 96%, 97%, 98%, or 99% in at least 60% of the patient population assayed, for example, in at least 65%, 70%, 75% or 80% of the patient population assayed. The weights can also be selected such that the accuracy of a method of the invention in a patient population having a liver fibrosis prevalence of up to 20% is at least about 80% and can be, for example, at least 85%, 90%, 91%, 92%, 93%, 94%, 95%, 96%, 97%, 98%, or 99% in at least 60% of the patient population assayed, for example, in at least 65%, 70%, 75% or 80% of the patient population assayed. Similarly, the weights can be selected such that the accuracy of a method of the invention in a patient population having a liver fibrosis prevalence of up to 30% is at least about 80% and can be, for example, at least 85%, 90%, 91%, 92%, 93%, 94%, 95%, 96%, 97%, 98%, or 99% in at least 60% of the patient population assayed, for example, in at least 65%, 70%, 75% or 80% of the patient population assayed.

Substantiation of the diagnosis may be affected using techniques such as imaging and biopsy. Following diagnosis, the subject is typically informed of the outcome either prior to or following the substantiation.

It is expected that during the life of a patent maturing from this application many novel liver markers will be discovered and the scope of the term liver marker is intended to include all such new technologies a priori.

As used herein the term "about" refers to ±10%

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Evaluation of sH2a, as a Potential Noninvasive Marker for Liver Fibrosis in Patients with Hepatitis C Materials and Methods MATERIALS: Immobilon-P paper was purchased from Millipore Corp. (Bedford, Mass.). Protein A-sepharose was from Repligen (Cambridge, Mass.). N-glycosydase-F was obtained from Boehringer Mannheim Biochemicals (Indianapolis, Ind.). Succinimidyl 4-(N-maleimidomethyl)cyclohexane-1-carboxylate and dimethylpimelidate were from Pierce (Rockford, Ill.). A solution of 3,3', 5,5'-tetramethylbenzidine (TMB) was purchased from Kirkegaard and Perry Laboratories Inc. (Gaithersburg, Md.). Alkaline phosphatase (ALP) substrate p-nitrophenylphosphate (p-NPP) was from Chemicon International (Temecula, Calif.).

Antibodies: Polyclonal antibodies specific for a peptide corresponding to the carboxyterminus of sH2a or to a peptide unique to sH2a (169 antibody) were described previously (Tolchinsky S, et al., J Biol Chem 1996; 271(24):14496-14503). A monoclonal antibody was prepared by intraperitoneal immunization of BALB/c mice with a conjugate of KLH with the carboxyterminal peptide of H2 (CEKRRNATGEVA-SEQ ID NO: 1) and complete Freunds adjuvant. Conjugation was performed using succinimidyl 4-(N-maleimidomethyl) cyclohexane-1-carboxylate. The hybridoma cells that resulted from fusion of the mouse splenocytes with NS/O myeloma cells were screened by ELISA, selecting a clone (B9) that reacted strongly with the peptide but not with KLH. B9 was analyzed using an Isostrip isotype test kit (Roche diagnostic corporation, Indianapolis, Ind.), indicating isotype IgG3. Ascitic fluid, obtained by injection of hybridoma cells to mice was used in all experiments due to difficulties in IgG3 purification by standard methods. It did not show any significant background.

Goat anti-mouse IgG or anti-rabbit IgG antibodies conjugated to ALP or to horseradish peroxidase were from Jackson Immunoresearch Laboratories (West Grove, Pa.).

Cell culture: NIH 3T3 cells and a stable transfectant expressing H2a (2-18 cell line) (Tolchinsky S, et al., J Biol Chem 1996; 271(24):14496-14503) were grown in DMEM supplemented with 10% newborn calf serum. HepG2 cells were grown in minimum Eagle's medium plus 10% fetal calf serum.

Immunoprecipitation and immunoblotting: Immunoprecipitations from cell supernatants (1.2-1.5 ml from 90 mm plates), using rabbit anti-H2a carboxyterminal or 169 antibodies were done as described before (Tolchinsky S et al., J Biol Chem 1996; 271(24):14496-14503). Immunoprecipitations from serum samples (0.2-0.3 ml) were done in a similar manner or using anti-H2a antibody crosslinked to protein A-sepharose with dimethylpimelidate where indicated. Immunoprecipitation with the B9 monoclonal antibody was followed by goat anti-mouse IgG bound to agarose. Treatment of immunoprecipitates with N-glycosidase-F and SDS-PAGE were done as described in Tolchinsky et al supra.

Immunoblotting was performed as described before (Kamhi-Nesher S. et al, Mol Biol Cell 2001; 12(6):1711-23) using anti-H2a carboxyterminal antibody and detection was performed with TMB solution or using the ECL procedure and a Bio-Rad ChemiDoc XRS system.

Competitive ELISA: Corning ELISA plate wells were coated with the carboxyterminal peptide of sH2a (5 µg/ml) and blocked with 3% BSA in Tris-buffered saline, pH 7.5 (TBS). Ascitic fluid containing B9 monoclonal antibody (1:1500) was preincubated overnight at 4° C. with serial dilutions of the serum sample. It was then added to the coated ELISA plate wells and incubated for 1 hour at RT. The wells were washed with TBS and reacted with goat anti-mouse IgG conjugated to ALP for 1 hour at RT. After reacting with the ALP substrate p-NPP, the OD was quantified using an ELISA reader at 405 nm.

Study subjects: Retrospective samples were from a group of healthy blood donors and a cohort of consecutive HCV-infected patients that had not yet received treatment. Patients co-infected with HIV, HBV or with additional diseases from other etiologies were excluded from the study. The study had a priori approval by the hospital ethical committee according to the Helsinki Declaration and written informed consent was obtained from all participants.

Routine laboratory tests: Patients had routine laboratory tests performed by a certified central lab, using common commercial methods. These tests included total bilirubin, ALP, ALT, AST, GGT, albumin, serum cholesterol, PT and HCV RNA level (reverse transcriptase polymerase chain reaction). Similar tests were done on healthy individuals except for PT and HCV RNA.

Liver histology: Percutaneous liver biopsy was performed using a Trucore 2 [R] biopsy instrument under ultrasound guidance. A single pathologist blinded to all clinical and serological results evaluated all slides. Two patients where biopsies were found inadequate were excluded from the study. Biopsies were METAVIR-scored (Bedossa P et al., Hepatology 1996; 24(2):289-93) for fibrosis stage and inflammation grade.

Statistical analysis: Comparison between groups of patients according to stage of disease with regard to demographic (age, gender) and clinical parameters was performed using Chi-square tests and Kruskal-Wallis non-parametric analysis of variance (ANOVA), as applicable. Additional analysis was performed with fibrosis stages grouped in two ways: (a) 2-3 vs. 0-1, (b) 3-4 vs. 0-2. The association between stage and other parameters was examined using logistic regression. Results are presented as odds ratio (OR), sensitivity and specificity with 95% confidence intervals (CI). The diagnostic value of the combination score of sH2a, ALT and AST with regard to fibrosis stages was evaluated by the area under the receiver operating characteristic curve (AUROC). The statistical significance level was set to 0.05. SPSS for Windows software, version 14.0 (Chicago, Ill.) was used for the analysis.

Results sH2a in human sera: To analyze whether sH2a is present in human serum, samples of normal human sera were subjected to immunoprecipitation with anti-H2a carboxyterminal antibody, treatment with N-glycosidase-F, SDS-PAGE and Western blotting with the same antibody (FIG. 1A, lanes 6-7 and 9). A band of about 28 kDa, similar in size to the one observed for sH2a in media from HepG2 cells was detected (FIG. 1A, lane 4). Media from a control cell line that does not express sH2a (NIH 3T3 cells) showed no signal (FIG. 1A, lanes 1 and 2). Without the N-glycosidase-F treatment, a disperse band of glycosylated sH2a of about 40 kDa is seen (lanes 3, 5 and 8), which probably represents heterogeneously glycosylated species. No H1 was detected in normal human serum (data not shown).

Development of an ELISA assay to quantify the serum levels of sH2a: For comparative analysis of the concentration of sH2a in serum, a new specific mouse monoclonal anti-peptide H2a antibody was developed. The hybridoma B9 produced a monoclonal antibody that recognized specifically sH2a secreted from transfected NIH 3T3 cells (2-18 cell line) or present in human serum (FIG. 1B). The B9 antibody was used to develop an ELISA assay based on the binding of this antibody to its peptide. The binding could be competed by 81% after pre-incubation of the antibody with a solution containing 0.5 µg/ml of the same peptide, but not of a control peptide. The binding could also be competed in a concentration-dependent manner by pre-incubation of the antibody with normal human serum; a 1:32 dilution of serum resulted in 50% reduction in the binding.

Comparison of the serum levels of sH2a in a cohort of HCV patients with those in healthy individuals: Using the ELISA assay described above, samples of serum obtained from 44 pretreatment HCV patients and from 28 healthy individuals were analyzed blindly and randomly, both populations had male and female individuals with a similar wide range of ages (see Table 2 for HCV patients and Table 3, for healthy individuals, herein below).

TABLE 2

| Characteristic | Median | [IQR] | range |
| --- | --- | --- | --- |
| Male (%) | 63.64 | | |
| Age | 41.5 | 29-53 | 19-64 |

TABLE 2-continued

| Characteristic | Median | [IQR] | range |
| --- | --- | --- | --- |
| Weight (kg) | 73 | 66-84 | 56-127 |
| total bilirubin (mg/dL) | 2 | 1-3 | 0.3-4 |
| bilirubin/normal* | 0.29 | 0.14-0.43 | 0.04-0.71 |
| ALP (U/L) | 75 | 62-96.5 | 44-194 |
| ALP/normal* | 0.63 | 0.50-0.77 | 0.36-1.50 |
| ALT (U/L) | 75 | 43-103 | 30-458 |
| ALT/normal* | 1.77 | 1.21-2.66 | 0.70-13.47 |
| AST(U/L) | 47 | 33-59 | 21-291 |
| AST/normal* | 1.31 | 0.96-1.67 | 0.58-8.56 |
| GGT (U/L) | 33 | 23-52 | 10-246 |
| GGT/normal* | 0.56 | 0.37-0.94 | 0.18-5.02 |
| albumin (gr/L) | 45 | 43-47 | 38-54 |
| albumin/normal* | 0.92 | 0.88-0.96 | 0.78-1.10 |
| serum cholesterol (mg/dL) | 166 | 142-199 | 102-323 |
| cholesterol/normal* | 0.83 | 0.71-1.00 | 0.51-1.62 |
| PT (sec) | 12 | 11.4-12.2 | 10.4-14.8 |
| PT/normal* | 0.81 | 0.77-0.82 | 0.70-0.99 |
| sH2a/normal** | 0.98 | 0.80-1.13 | 0.21-1.60 |
| Fibrosis stage | 1 | 0-3 | 0-4 |
| Inflammation grade | 2 | 1-3 | 0-4 |

*Median of absolute values divided by upper limit of normal range
**Median of absolute values divided by absolute value of a standard batch of healthy human serum.

TABLE 3

| Characteristic | Median | [IQR] | range |
| --- | --- | --- | --- |
| Male (%) | 53.57 | | |
| Age | 40.00 | 29-48 | 22-64 |
| total bilirubin (mg/dL) | 0.36 | 0.22-0.50 | 0.06-1.05 |
| bilirubin/normal | 0.05 | 0.05-0.16 | 0.009-0.42 |
| ALP (U/L) | 48.00 | 36-55 | 22-88 |
| ALP/normal | 0.35 | 0.33-0.51 | 0.17-0.68 |
| ALT (U/L) | 19.00 | 14-27 | 9-38 |
| ALT/normal | 0.42 | 0.37-0.65 | 0.26-1.03 |
| AST(U/L) | 27.00 | 20-31 | 14-39 |
| AST/normal | 0.67 | 0.49-0.89 | 0.35-1.08 |
| GGT (U/L) | 12.50 | 3-18 | 1-38 |
| GGT/normal | 0.18 | 0.06-0.38 | 0.02-0.62 |
| albumin (g/L) | 43.00 | 41-46 | 31-50 |
| albumin/normal | 1.24 | 1.20-1.39 | 0.89-1.52 |
| serum cholesterol (mg/dL) | 190.00 | 167-219 | 101-274 |
| cholesterol/normal | 0.86 | 0.83-1.09 | 0.50-1.37 |
| sH2a/normal | 1.00 | 0.92-1.10 | 0.71-1.27 |

HCV patients had biopsies taken that gave a median METAVIR—fibrosis stage of 1 and ranges 0-4. The samples were also analyzed for a series of routine liver tests. Only the median levels of ALT and AST were above the normal, whereas bilirubin, ALP, GGT, albumin and cholesterol were in the normal range for both populations. The median PT, measured for the HCV patients, was also in the normal range (Table 2). The levels of sH2a, measured in comparison to those of a large standard batch of serum from a healthy individual, were quite constant for the healthy group, giving a median of 1.00 (level: normal level), with a range of 0.71-1.27 (interquartile range (IQR): 0.92-1.10) (Table 3). For the HCV patients the sH2a median was similar, 0.98, but the range was much wider, 0.21-1.60 (Table 2).

Next, the relation between levels of the different markers and fibrosis stage was analyzed (see Table 4—Univariate analysis of correlation of characteristics with advanced fibrosis).

TABLE 4

| Characteristic | Healthy N (n = 28) | HCV patients Fibrosis stage | | P value | Odds ratio (95% CI) |
| --- | --- | --- | --- | --- | --- |
| | | 0-2 (n = 31) | 3-4 (n = 13) | | |
| Male gender* | 15 (53.6) | 18 (58.1) | 10 (76.9) | 0.235 | 2.41 (0.55-10.52) |
| Median age (IQR) | 40 (29-48) | 35 (27-49) | 51 (47-55) | 0.019 | 1.08 (1.01-1.16) |
| bilirubin/normal >1 | 0 (0) | 0 (0) | 0 (0) | — | — |
| ALP/normal >1 | 0 (0) | 1 (3.23) | 3 (23.1) | 0.027 | 10.00 (0.92-108.33) |
| ALT/normal >2 | 0 (0) | 10 (32.3) | 8 (61.5) | 0.047 | 4.20 (1.09-17.32) |
| AST/normal >1 | 1 (3.6) | 18 (58.1) | 12 (92.3) | 0.008 | 9.33 (1.81-48.24) |
| GGT/normal >1 | 0 (0) | 5 (16.1) | 5 (38.5) | 0.075 | 3.71 (0.83-16.55) |
| albumin/normal <0.8 | 0 (0) | 1 (3.23) | 0 (0) | 0.529 | 1.4 (1.16-1.70) |
| cholesterol/normal >1.2 | 2 (7.1) | 1 (3.23) | 1 (7.69) | 0.476 | 2.73 (0.16-47.46) |
| abnormal sH2a (<0.85 or >=1.2) | 6 (21.4) | 11 (35.5) | 9 (69.2) | 0.040 | 4.09 (1.02-16.40) |

There was a moderate increase in the likelihood for very high levels of ALT (>twice the upper limit of the normal range) in patients with increasing fibrosis stage. There was a significant increase in the likelihood for high levels of ALP although the percent of patients at fibrosis stages 3-4 with high ALP was still low (23%). There was a stronger correlation between the levels of AST and GGT with fibrosis stage. There was also a strong correlation of likelihood for abnormal sH2a levels with increasing fibrosis stage. This abnormal sH2a range was taken as <0.85 or >=1.20 fold that of the normal standard sample (equal to the median of the healthy population (=1)). Most individuals with abnormal sH2a had a decreased level of the marker in serum, but a few (7) presented an abnormally high level. There was considerable difference in the percent of individuals with abnormal sH2a between the group with mild or moderate fibrosis (stages 0-2) (35.5%) to those with advanced fibrosis (stages 3-4) (69.2%) (Table 4). As shown in FIG. 2A, there was a steady increase in the number of individuals with an abnormal level of sH2a with increasing fibrosis stage. All patients at stage 4 showed abnormal sH2a levels, but because of the small number of samples at this stage they were joined with those at stage 3 to achieve statistical significance (FIG. 2A). Most noteworthy, sH2a shows a change to abnormal levels in a significant portion of patients at intermediate fibrosis stages (1-2). To obtain a ROC plot for sH2a one must take into consideration abnormal values that are above or below the normal range. Therefore an sH2a score was calculated as follows: sH2a score=1 if normalized sH2a 0.85-1.19, 2 if normalized sH2a 0.76-0.84 or 1.20-1.40, 3 otherwise. The AUROC obtained with sH2a scores for advanced fibrosis was 0.724 (FIG. 2B).

A combined score of the levels of sH2a, ALT and AST: Given that sH2a levels would reflect liver function, whereas the levels of ALT and AST are indicative of liver damage, it was reasoned that a combination of these values would compensate for individual fluctuations in the overall state of each patient, giving an improved correlation to fibrosis. Indeed, an algorithm combining the levels of sH2a with those of ALT and AST gave a score that was statistically predictive of the stage of fibrosis (FIG. 2C). The combined value was calculated as follows: Combined score=(1 if average (avg) of normalized (ALT,AST)<1.1, 2 if avg of normalized (ALT,AST) 1.1-2, 3 otherwise)×(2 if normalized sH2a 0.85-1.19, 4 if normalized sH2a 0.76-0.84 or 1.20-1.40, 6 otherwise)−2.

Using this combined value, the AUROC calculated for advanced fibrosis (stages 3-4) was very high, 0.880 (FIG. 2D) with sensitivity of 91.7% and specificity of 75.0%. The AUROC was also high, 0.846, when calculated for intermediate-significant fibrosis (stages 2-3) (FIG. 2E).

Discussion

The present inventors suggest that sH2a is a marker of liver function, possibly correlating to the mass of functional hepatocytes (FIG. 3). Reduction of the levels of sH2a could reflect early events in the fibrogenic process, affecting hepatocyte function. The few cases where sH2a levels were abnormally high might indicate the start of a neoplastic process with proliferation of hepatocytes that express high levels of the ASGPR. On the other hand, during the evolution of fibrosis, temporary changes in the total hepatocyte function (indicated by sH2a levels) may not occur simultaneously with changes in the release and clearance of damage markers (ALT, AST). The function (sH2a) and damage markers give complementary information and when combined provide an accurate prediction of the fibrosis stage, including early and intermediate stages of fibrosis that other markers fail to detect (FIG. 2). In the combined algorithm of the present invention, the higher weight given to sH2a reduces the influence of ALT and AST variations due to non-hepatic sources.

The combination of sH2a, ALT and AST gave an AUROC of 0.846 for intermediate fibrosis (stages 2-3), which is unmatched by other markers or combinations of markers. For advanced fibrosis and cirrhosis (stages 3-4) the AUROC obtained was 0.880, which compares very favorably with the AUROC obtained with combinations of other markers, e.g. AUROC=0.76 for significant fibrosis and AUROC=0.82 for cirrhosis in an AST to platelet ratio (Shaheen A A, Myers R P. Hepatology 2007; 46(3):912-21), AUROC=0.81 for cirrhosis with combined HA, TIMP-1, and platelet count (Fontana R J, Hepatology 2008; 47(3):789-98) and AUROC=0.84 with Fibrotest (Poynard T, et al. BMC Gastroenterol 2007; 7:40).

The sensitive assessment of hepatocyte function by sH2a would also be very useful in measuring success of patient treatment.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method of staging a liver fibrosis in a subject, the method comprising:

(a) determining a level of sH2A, alanine aminotransferase (ALT) and aspartate aminotransferase (AST) in a sample of the subject;

(b) scoring a change with respect to a sample from a healthy individual in said sH2A;

(c) scoring an upregulation of said ALT and said AST with respect to a sample from a healthy individual; wherein a combined score of said sH2A, ALT and AST is indicative of the stage of the liver fibrosis.

2. The method of claim 1, wherein said sample is selected from the group consisting of blood, urine and saliva.

3. The method of claim 1, wherein a change in said sH2A is an up-regulation.

4. The method of claim 1, wherein a change in said sH2A is a down-regulation.

5. The method of claim 1, wherein a score of a normalized level of said sH2A is at least twice the score of a normalized level of an average of said ALT and said AST.

6. The method of claim 1, wherein the staging is effected by:
   (a) calculating an average of a normalized ALT level and a normalized AST level to obtain a normalized average ALT/AST value;
   (b) indexing said normalized average ALT/AST value, wherein a normalized average value of less than 1.1 is equivalent to an index of 1, a normalized average value of 1.1-2 is equivalent to an index of 2 and a normalized average value greater than 2 is equivalent to an index of 3;
   (c) calculating a normalized sH2A level to obtain a normalized sH2A value; and
   (d) indexing said normalized sH2A value, wherein a normalized sH2A value of 0.85-1.19 is equivalent to an index of 2, a normalized sH2A value of 0.76-0.84 or 1.20-1.40 is equivalent to an index of 4 and a normalized sH2A value of less than 0.76 or greater than 1.46 is equivalent to an index of 6; and
   (e) staging said liver fibrosis according to formula 1 [ALT/AST index×sH2A index]−2;

wherein a result of about 1 is indicative of a stage 0 of liver fibrosis;
a result of about 2 is indicative of a stage 1 of liver fibrosis;
a result of about 4 is indicative of a stage 2 of liver fibrosis;
a result of about 7 is indicative of a stage 3 of liver fibrosis; and
a result of about 11 is indicative of a stage 4 of liver fibrosis.

* * * * *

SEQUENCE LISTING

```
<160> NUMBER OF SEQ ID NOS: 2

<210> SEQ ID NO 1
<211> LENGTH: 12
<212> TYPE: PRT
<213> ORGANISM: Artificial sequence
<220> FEATURE:
<223> OTHER INFORMATION: Carboxyterminal peptide of H2 used for
      immunization and Ab preperation

<400> SEQUENCE: 1

Cys Glu Lys Arg Arg Asn Ala Thr Gly Glu Val Ala
1               5                   10

<210> SEQ ID NO 2
<211> LENGTH: 233
<212> TYPE: PRT
<213> ORGANISM: Homo sapiens

<400> SEQUENCE: 2

Ser Gln Ser Glu Gly His Arg Gly Ala Gln Leu Gln Ala Glu Leu Arg
1               5                   10                  15

Ser Leu Lys Glu Ala Phe Ser Asn Phe Ser Ser Ser Thr Leu Thr Glu
                20                  25                  30

Val Gln Ala Ile Ser Thr His Gly Gly Ser Val Gly Asp Lys Ile Thr
            35                  40                  45

Ser Leu Gly Ala Lys Leu Glu Lys Gln Gln Asp Leu Lys Ala Asp
        50                  55                  60

His Asp Ala Leu Leu Phe His Leu Lys His Phe Pro Val Asp Leu Arg
65                  70                  75                  80

Phe Val Ala Cys Gln Met Glu Leu Leu His Ser Asn Gly Ser Gln Arg
                85                  90                  95

Thr Cys Cys Pro Val Asn Trp Val Glu His Gln Gly Ser Cys Tyr Trp
            100                 105                 110

Phe Ser His Ser Gly Lys Ala Trp Ala Glu Ala Glu Lys Tyr Cys Gln
        115                 120                 125

Leu Glu Asn Ala His Leu Val Val Ile Asn Ser Trp Glu Glu Gln Lys
130                 135                 140

Phe Ile Val Gln His Thr Asn Pro Phe Asn Thr Trp Ile Gly Leu Thr
145                 150                 155                 160

Asp Ser Asp Gly Ser Trp Lys Trp Val Asp Gly Thr Asp Tyr Arg His
                165                 170                 175

Asn Tyr Lys Asn Trp Ala Val Thr Gln Pro Asp Asn Trp His Gly His
            180                 185                 190

Glu Leu Gly Gly Ser Glu Asp Cys Val Glu Val Gln Pro Asp Gly Arg
        195                 200                 205

Trp Asn Asp Asp Phe Cys Leu Gln Val Tyr Arg Trp Val Cys Glu Lys
    210                 215                 220

Arg Arg Asn Ala Thr Gly Glu Val Ala
225                 230
```